(12) United States Patent
Makovec et al.

(10) Patent No.: US 7,145,037 B2
(45) Date of Patent: Dec. 5, 2006

(54) ADAMANTANE DERIVATIVES WITH NEUROPROTECTIVE, ANTIDEPRESSANT AND ANTI-ISCHAEMIC ACTIVITIES, AND PROCESS FOR PREPARING THEM

(75) Inventors: Francesco Makovec, Lesmo (IT); Roberto Artusi, Rho Milan (IT); Simona Zanzola, Milan (IT); Lucio Claudio Rovati, Monza (IT)

(73) Assignee: Rotta Research Laboraturium S.p.A., Milan (IT)

( * ) Notice: Subject to any disclaimer, the term of this patent is extended or adjusted under 35 U.S.C. 154(b) by 0 days.

(21) Appl. No.: 10/931,245

(22) Filed: Sep. 1, 2004

(65) Prior Publication Data

US 2005/0049312 A1    Mar. 3, 2005

(30) Foreign Application Priority Data

Sep. 2, 2003    (IT)    ............................ TO2003A0668

(51) Int. Cl.
*C07C 257/00* (2006.01)
*C07C 279/00* (2006.01)
*A61K 31/155* (2006.01)

(52) U.S. Cl. ...................... 564/225; 564/230; 514/631; 514/634

(58) Field of Classification Search ................ 564/230, 564/225; 514/634, 631
See application file for complete search history.

(56) References Cited

U.S. PATENT DOCUMENTS

| 4,007,181 A * | 2/1977 | DuCharme et al. ......... 544/165 |
| 5,061,703 A | 10/1991 | Bormann et al. |
| 2002/0028836 A1 | 3/2002 | Altenbach et al. |

FOREIGN PATENT DOCUMENTS

| DE | 1 943 404 | 12/1970 |
| GB | 1 274 652 A | 5/1972 |
| WO | WO 91/18868 A1 | 12/1991 |
| WO | WO 99/20599 A1 | 4/1999 |
| WO | WO 99/31051 A | 6/1999 |
| WO | WO 99/38841 A | 8/1999 |
| WO | WO 99/42458 A1 | 8/1999 |
| WO | WO 02/070468 A | 9/2002 |
| WO | WO 03/024401 A2 | 3/2003 |

OTHER PUBLICATIONS

Westland et al, J. med Chem., 1972, vol. 15, No. 12, 1313-1321.*
Database Chemcats Online Chemical Abstracts Service., Columbus, Ohis, US; XP002305001, retrieved from STN Databse Accession No. 2001:2447512 RN 313376-00-0 & "Pharma Library Collection (Catalog)" Apr. 24, 2003, Ordre No. NS64016.
Novakov, I.A., et al, Khim.Farm. Zh., Supplied by British Library—"The World's Knowledge" www.bl.uk 1987, pp. 454-458, vol. 21(4).
Bernatowicz, M.S., et al., 1*H*-Prazole-1carboxamidine Hydrochlorine: An Attractive Reagent for Guanylation of Amines and Its Application to Peptide Synthesis, J. Org. Chem. Soc., 1992, pp. 2497-2502, vol. 57.
McKay, A.F., The Preparation of N-Substituted-$N^1$-nitroguanidines by the Reaction of Primary Amines with N-Alkyl-N-nitroso-$N^1$-nitroguanidines[1], J. Am. Chem. Soc., Contribution from the Departement of Chemistry, Queens University, 1949, pp. 1968-1970, vol. 71.
Foster et al., The Novel Anticonvulsant MK-801 Binds to the Activated State of the N-methyl-D-aspartate Receptor in Rat Brain, Br. J. Pharmacol. 1987, pp. 403-409, vol. 91.
Zablocka et al., PAF Antagonist, BN52021, Inhibits [$^3$H]D-Aspartate Release After Ischaemia in Vitro NeuroReport 6, 1994, vol. 6, No. 1, pp. 85-88.
Berenbaum et al, Insulin-Like Growth Factors Counteract the Effect of Interleukin 1β on Type II Phospholipase A2 Expression and Arachidonic Acid Release by Rabbit Articular Chondrocytes, FEBS Letters, 1994, vol. 340, pp. 51-55.
Green et al., Analysis of Nitrate, Nitrite, and [$^{15}$N]Nitrate in Biological Fluids, Analytical Biochemistry, 1982, vol. 126, pp. 131-138.
Porsolt et al., Behavioural Despair in Mice: A Primary Screening Test for Antidepressants, Arch. Int. Pharmacodyn. 1977, vol. 229, pp. 327-336; and.
Steru et al., The Tail Suspension Test: A New Method for Screening Antidepressants in Mice, Psychopharmacology 1985, vol. 85, pp. 367-370.

* cited by examiner

*Primary Examiner*—Shailendra Kumar
(74) *Attorney, Agent, or Firm*—Sughrue Mion, PLLC

(57) ABSTRACT

The invention describes compounds represented by the general formula (I) given below:

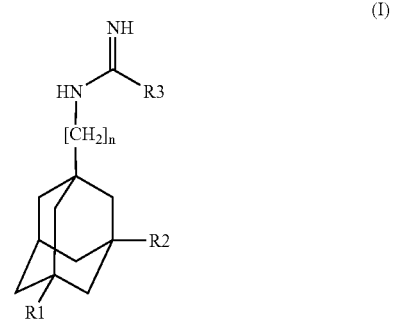

(I)

in which:
n is an integer between 1 and 4;
$R_1$ and $R_2$ are chosen independently from hydrogen and a methyl group;
$R_3$ is chosen independently from a linear, branched or cyclic alkyl group containing from 1 to 3 carbon atoms ($R_{3a}$) and a simple amino group ($R_{3b}$) or an amino group substituted with a nitro group ($R_{3c}$) The compounds are useful for treating central nervous system diseases or peripheral neuropathies.

10 Claims, No Drawings

ADAMANTANE DERIVATIVES WITH NEUROPROTECTIVE, ANTIDEPRESSANT AND ANTI-ISCHAEMIC ACTIVITIES, AND PROCESS FOR PREPARING THEM

BACKGROUND OF THE INVENTION

The present invention relates to novel amidine and guanidine derivatives of adamantane that may be represented by the general formula (I) given below:

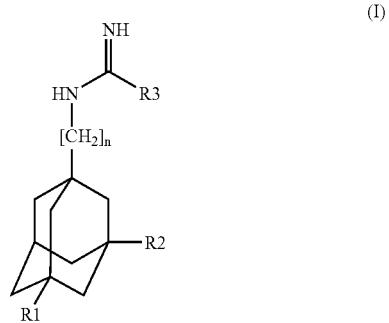

in which:
- n is an integer between 1 and 4;
- $R_1$ and $R_2$ are chosen independently from hydrogen and a methyl group;
- $R_3$ is chosen independently from a linear, branched or cyclic alkyl group containing from 1 to 3 carbon atoms ($R_{3a}$) and a simple amino group ($R_{3b}$) or an amino group substituted with a nitro group ($R_{3c}$), and pharmaceutically acceptable salts thereof.

SUMMARY OF THE INVENTION

The compounds that are the subject of the invention are non-competitive receptor antagonists for the NMDA receptor and may have a favourable use either for treating central nervous system (CNS) diseases, for instance Alzheimer's disease, senile dementia, cerebral ischaemia and depression, or for treating neuropathic peripheral forms, these pathologies possibly being correlated at least partially with dysfunction of the glutamatergic system.

The NMDA receptor belongs the family of glutamic acid ionotropic receptors, along with the AMPA receptor and the kainate receptor. The various NMDA receptors present in the central nervous system are differentiated by the composition of the protein subunits (NR1, NR2$_{A-D}$, NR3) that form the calcium channel that distinguishes the receptor. The binding sites for glutamic acid (agonist) and glycine (co-agonist) are present on the extracellular portion of the receptor. In addition, at least another two modulatory sites outside the channel (polyamine and zinc) and two inside the channel (MK-801 and $Mg^{2+}$) are present.

Calcium influx into the NMDA channel takes place, under physiological conditions, when a glutamatergic presynaptic neurone releases, following an action potential, glutamic acid molecules into the synapse. The released glutamate interacts with the catalytic site of the NMDA receptor on the post-synaptic neurone and, once the channel is freed of the magnesium that occupies it under rest conditions, allows calcium influx from the extracellular medium into the intracellular medium.

If the calcium channel associated with the NMDA receptor remains open to the calcium influx for more than a few milliseconds (pathological condition), a cascade of intracellular reactions is initiated, leading to neuronal death (apoptosis). Therapeutic intervention may thus take place either by blocking the influx of calcium ions or by interacting with the NMDA receptor binding sites.

The effects of the compounds according to the invention were studied in preclinical pharmacology both in vitro and in vivo.

In vitro, some of them have been demonstrated to inhibit, on rat hippocampus noradrenergic neurones, NMDA-induced receptor activation in a sub-micromolar concentration range.

Some of the compounds forming the subject of the invention have also been demonstrated to increase the basal release of noradrenalin (NE) in rat hippocampus slices, and to increase in the corpus striatum both the basal release of dopamine and that of acetylcholine. Some of them have been demonstrated to block the release of aspartate evoked by an ischaemic insult.

The compounds that are the subject of the invention have also been demonstrated to be inhibitors of inducible NO (nitric oxide) synthetase (iNOS). This enzyme, which is induced either in the presence of numerous pro-inflammatory cytokines or by endotoxin, is expressed in various types of cells, for instance neutrophils and macrophages.

Thus, the compounds according to the invention may also be advantageously used in inflammatory diseases, for instance rheumatoid arthritis. Their combined antagonist activity on the NMDA receptor and on the enzyme iNOS may be useful in the treatment of peripheral neuropathies either of mechanical origin (compressions, contusions, fractures, etc.) or metabolic origin, such as in the case of diabetes mellitus, and for treating a neurological syndrome known as "AIDS dementia-complex", characterized both by diffuse neuronal loss of the CNS and by impairment of the mechanisms of learning and memorization and of motor control.

The neuroprotective effect of the compounds that are the subject of the invention may also be used successfully in the treatment and prevention of ischaemic cerebral pathologies.

The compounds that are the subject of the invention have been demonstrated to have antidepressant activity, according to various experimental models on mice that are acknowledged as valid models for evaluating the antidepressant activity of a drug.

Thus, by virtue of their particular mechanism of action, which consists of the capacity to modulate the activation of the NMDA receptor complex and the noradrenergic, dopaminergic and cholinergic systems and of the inhibition of the enzyme iNOS, the above mentioned compounds may be advantageously used in the treatment and prevention of various diseases associated with a deterioration in or poor functioning of the cognitive capacities, for instance disturbances in mental capacity, organic and senile cognitive deterioration, Alzheimer's disease, senile dementia, AIDS dementia-complex, behavioural disturbances and depression, for the treatment of peripheral neuropathies of any origin and in cerebral ischaemia.

A large number of studies have been performed in the last ten years in the search for drugs for treating dementias in general and Alzheimer's disease in particular. Among these drugs, a particular role is played by memantine, an aminoadamantyl derivative. Developed in the 1980s as an anti-Parkinsonian drug for its dopaminomimetic activity, it was subsequently found that this substance was capable of blocking the flow of calcium ions across the NMDA receptor-associated channel at concentrations up to 100 times lower than those required to promote the release of dopamine at cortico-striatol levels. On the basis of these results, memantine was reconsidered as a potential drug for treating Alzheimer's disease. However, although memantine has activity comparable to the compounds that are the subject of the invention for inhibiting the receptor binding of MK-801 and for inhibiting the NE-evoked release of NMDA in the hippocampus, it is markedly less active in the basal release of NE in the hippocampus and entirely inactive in the basal release of Ach in the corpus striatum, just as it is entirely inactive in inhibiting the inducible enzyme iNOS.

As mentioned above, there is ample patent literature relating to therapeutic activity for various classes of adamantane amino derivatives apart from memantine itself: thus, for example, DE 19 43 404 from 1971 claims and describes compounds with antidepressant activity; US 2002/028836 refers to derivatives with activity as "potassium-channel openers"; WO99/42458 claims and describes compounds having high affinity for the histaminic $H_3$ receptor; WO99/20599 describes adamantyl derivatives for treating neurodegenerative disorders; WO91/18868 describes novel Sigma receptor ligands; WO03/024401 refers to novel chemochemical receptor modulators; U.S. Pat. No. 5,061,703 (from 1991) claims amino-adamantyl derivatives for preventing and treating ischaemia.

However, none of the cited patents claims adamantane derivatives substituted with amidine or guanidine groups and is suitable for inserting these groups, which has given the possibility of simultaneously modulating the overactivation of the NMDA receptor complex with inhibition of the enzyme iNOS and with an increase in the basal release of the mediators NE, acetylcholine and dopamine.

The process for preparing the derivatives that are the subject of the invention illustrated by formula I consists of the following operations, which may be summarized as follows: reacting the suitably substituted adamantylalkylamine of general formula (II) (see the general synthetic scheme), obtained via a known literature procedure: (see, for example: Novakov, I. A.; et al. *Khim.-Farm. Zh.*, 1987, 21(4), 454–458) and in which $R_1$, $R_2$ and n have the meaning given above, with a series of reagents, namely:

a) alkylacetamidate of formula (IIIA) salified in hydrochloride form, in which $R_{3a}$ has the meaning given above; the reaction takes place in the presence of an excess of (IIIA) relative to (II) (preferably 2 mol to 1) and in the presence of a stoichiometric amount relative to (IIIA) of a tertiary base, preferably triethylamine, in an anhydrous inert solvent, for instance tetrahydrofuran, at a temperature of between 4° C. and the boiling point of the solvent, for a time of between 2 and 72 hours, to give the corresponding final derivatives of formula (IA) in which $R_1$, $R_2$, $R_{3a}$ and n have the meaning given above (see the general synthetic scheme, step a);

b) 1H-pyrazolo-1-carboxamidinium of formula (IIIB) salified in hydrochloride form, in which $R_{3b}$ has the meaning given above, in stoichiometric amount relative to (II) in an inert solvent, for instance acetonitrile, in the presence of a tertiary base, at a temperature of between 10° C. and the boiling point of the solvent for a time of between 2 and 72 hours, to give the corresponding final derivatives of formula (IB) in which $R_1$, $R_2$ and n have the meaning given above and $R_{3b}$ is an amino group (see the general synthetic scheme, step b); and c) N-methyl-N-nitroso-N'-nitroguanidine of formula (IIIC) in which $R_{3c}$ has the meaning given above. The reaction takes place in the presence of a deficit of (IIIC) relative to (II) (preferably 1 mol to 1.3) in an inert solvent, for instance ethyl ether, at a temperature of between 5° C. and the boiling point of the solvent for a time of between 2 and 72 hours, to give the corresponding final derivatives of formula (IC) in which $R_1$, $R_2$ and n have the meaning given above and $R_{3c}$ is a nitroamine group (see the general synthetic scheme, step c).

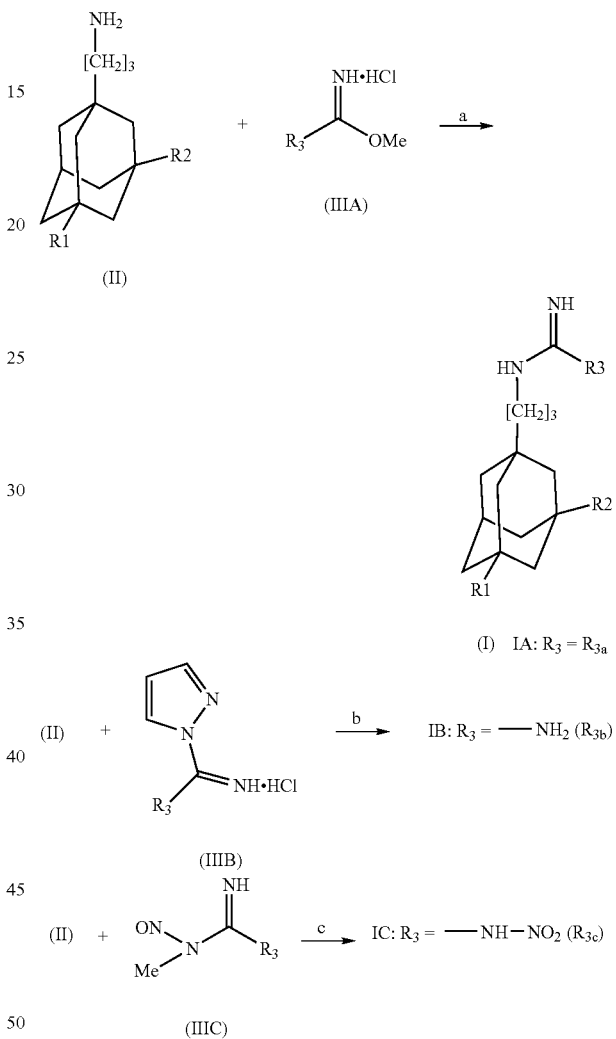

The examples that follow are given to illustrate the invention more clearly.

EXAMPLE 1

Preparation of
N-[2-(3,5-dimethyl-1-adamantyl)ethyl]-acetamidine
(compound 2 of Table 1)

1.7 g of 1-[2-(3,5-dimethyl-1-adamantyl)ethyl]amine (8.20 mmoles) are suspended in 50 ml of tetrahydrofuran. 2.3 ml of triethylamine (16.4 mmoles) and 1.73 g of methylacetamidate hydrochloride (16.4 mmoles) are added, with stirring at room temperature; the pH of the suspension is about 9. After 24 hours (the pH falls to 7), the solid is filtered off, washing with a small amount of tetrahydrofuran and ethyl ether. The residue taken up in water is basified with 4N sodium hydroxide solution to pH 11 and stirred for 1 hour, and then filtered off, washed with water and ethyl ether, and dried under vacuum over phosphorus pentoxide. The solid obtained is suspended in isopropyl ether and acidified with an 8M solution of HCl in isopropyl ether to give the hydrochloride (2.1 g), and is then filtered off, washed with isopropyl ether and recrystallized from acetonitrile. 1.9 g are obtained.

Formula: $C_{16}H_{29}ClN_2$ (MW 284.87). 80% yield.
TLC: (5/2/2 butanol/acetic acid/water) rf 0.78. M.p. 169° C.
$^1$HNMR (DMSO-$d_6$), ppm: 0.85 (s, 6H); 1.05–1.50 (m, 15H); 2.18 (s, 3H); 3.20 (m, 2H); 9.08 (bs, 3H).

All the derivatives of formula IA (see Scheme 1) are prepared in a similar manner using the appropriate alkylacetamidate.

EXAMPLE 2

Preparation of N-[2-(3,5-dimethyl-1-adamantyl)ethyl]guanidine (compound 4 of Table 1)

1.7 g of 1-[2-(3,5-dimethyl-1-adamantyl)ethyl]amine (8.20 mmoles) are suspended in 50 ml of acetonitrile. 1.14 ml of triethylamine (8.20 mmoles) and 1.2 g of 1H-pyrazolo-1-carboxamidinium hydrochloride (8.20 mmoles, Bernatowicz, M. S. et al. *J. Org. Chem.*, 1992, 57, 2497–2502) are added, with stirring at room temperature. The suspension is heated at 70° C. for 6 hours, left at room temperature for 24 hours and cooled to 0° C. The solid that precipitates out is filtered off, washed with acetonitrile, suspended in isopropyl ether and acidified with an 8M solution of HCl in isopropyl ether to give the hydrochloride, which is then filtered off, washed with isopropyl ether and recrystallized from acetonitrile. 1.5 g are obtained.

Formula: $C_{15}H_{28}ClN_3$ (MW 285.85). 65% yield.
TLC: (5/2/2 butanol/acetic acid/water) rf 0.83. M.p. 181° C.
$^1$HNMR (DMSO-$d_6$), ppm: 0.82 (s, 6H); 1.05–1.45 (m, 15H); 3.10 (m, 2H); 7.25 (bs, 4H); 7.80 (bs, 1H).

All the derivatives of formula (IB) in which $R_3$ is an amino group are prepared in a similar manner.

EXAMPLE 3

Preparation of N-[2-(3,5-dimethyl-1-adamantyl) ethyl]-nitroguanidine (compound 6 of Table 1)

1.4 g of 1-[2-(3,5-dimethyl-1-adamantyl)ethyl]amine (6.87 mmoles) are dissolved in 16 ml of a 3/1 ethyl ether/water mixture and 0.8 g of N-methyl-N-nitroso-N'-nitroguanidine (5.28 mmoles, McKay, A. F. *J. Am. Chem. Soc.* 1949, 71, 1968–1970) are added portionwise with stirring, while keeping the temperature below 22° C. The evolution of gas and formation of a precipitate are observed. After half an hour at room temperature, the solid is filtered off, washed with ethyl ether and recrystallized from 95% ethanol (50 ml/g). 1.5 g are obtained.

Formula: $C_{15}H_{26}N_4O_2$ (MW 294.39). 96.5% yield.
TLC: (85/25/2/1 chloroform/methanol/water/aqueous ammonia) rf 0.75. M.p. 205° C.
$^1$HNMR (DMSO-$d_6$), ppm: 0.75 (s, 6H); 0.98–1.45 (m, 15H); 3.05 (m, 2H); 7.80 (bs, 3H).

All the derivatives of formula (IC) in which $R_3$ is a nitroamine group are prepared in a similar manner.

A number of derivatives, obtained according to the invention, are given in Table 1 below, along with a number of physicochemical characteristics that identify them.

TABLE 1

Compounds of structure:

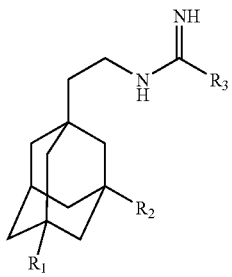

| Compound | $R_1$ | $R_2$ | $R_3$ | Empirical formula | m.p. (crystallization solvent)* | TLC $(R_f)$** |
|---|---|---|---|---|---|---|
| 1 | H | H | $CH_3$ | $C_{14}H_{24}N_2 \cdot HCl$ | 243 (A) | 0.72 (I) |
| 2 | $CH_3$ | $CH_3$ | $CH_3$ | $C_{16}H_{28}N_2 \cdot HCl$ | 169 (A) | 0.78 (I) |
| 3 | H | H | $NH_2$ | $C_{13}H_{23}N_3 \cdot HCl$ | 246 (A) | 0.83 (I) |
| 4 | $CH_3$ | $CH_3$ | $NH_2$ | $C_{15}H_{27}N_3 \cdot HCl$ | 181 (A) | 0.83 (I) |
| 5 | H | H | $NHNO_2$ | $C_{13}H_{22}N_4O_2$ | 260 (B) | 0.75 (II) |
| 6 | $CH_3$ | $CH_3$ | $NHNO_2$ | $C_{15}H_{26}N_4O_2$ | 205 (B) | 0.75 (II) |
| 7 | Me | Me | cyclopropyl | $C_{18}H_{30}N_2$ | 96 (A) | 0.66 (I) |

*Crystallization solvent: A (acetonitrile); B (95% ethanol).
**Eluent: (I) butanol/acetic acid/water (5/2/2) (v/v); (II) chloroform/methanol/water/aqueous ammonia (85/25/2/1) (v/v).

The following compounds were also synthesized in a manner similar to that in Example 1:

N-[1-(1-adamantyl)methyl]acetamidine
N-[4-(1-adamantyl)butyl]acetamidine

N-[2-(3-methyl-1-adamantyl)ethyl]acetamidine
N-[3-(1-adamantyl)propyl]acetamidine while the following compounds were synthesized in a manner similar to that given in Example 2:
N-[2-(3-methyl-1-adamantyl)ethyl]guanidine
N-[3-(1-adamantyl)propyl]guanidine In Vitro Pharmacological Activity Studies of Binding to Rat Cortical Synaptosomial Membranes The affinity of the compounds according to the invention for the NMDA receptor was evaluated by means of binding studies using as tracer the compound MK-801, which is a compound endowed with anticonvulsivant activity, which acts as a potent, selective and non-competitive NMDA antagonist.

Rat synaptosomial membrane preparations were used, with slight changes to the method described by Foster et al. [(Br. J. Pharmacol. 91, 403–409 (1987)]. Briefly, cortical membranes were incubated together with the tracer $H^3$-MK-801 for 45 minutes at 23° C. together with the test compounds. The reaction was terminated by separating the bound radioligand from the free radioligand, by filtration on glass fibre filters, which, after washing, were placed in contact with a liquid scintillator (β-counter), thus determining the radioactivity bound to the pellet. The specific binding is determined as the difference between the binding in the absence and in the presence of cold $10^{-4}$M MK-801.

The results thus obtained are expressed as $IC_{50}$, i.e. the concentration (in μmoles/liter) of the antagonist that is capable of displacing 50% of the ligand (MK-801) from the receptor. From the data obtained, it may be deduced that some of the compounds that are the subject of the invention show appreciable inhibitory activity on the binding of MK-801 to the rat cortical membrane receptors.

For example, compound 2 and compound 4 showed a displacing capacity of about 40 μM.

Memantine, a comparative non-competitive antagonist NMDA drug, was slightly less active under the same experimental conditions ($IC_{50}$ 80 μM)

Studies on Rat Cerebral Slices in Perfusion a) Studies on the Basal Release of Tritiated Neurotransmitters from Rat Cerebral Slices The animals were sacrificed and the brains rapidly removed from the brain case and immediately transferred at 4° C. into artificial cerebrospinal fluid (aCSF) aerated with a gas mixture composed of 95% oxygen and 5% carbon dioxide. The brains were then sectioned at a temperature of 4° C. and the encephalic areas of interest (hippocampus and corpora striata) removed and immersed in the solution mentioned above.

Cerebral slices 400 μm thick were then prepared using a McIllwain "chopper". The hippocampus slices were incubated with 0.08 μM of [$^3$H] noradrenalin and the striatum slices with 0.01 μM of [$^3$H] dopamine and/or with 0.09 μM of [$^3$H] choline at a temperature of 37° C. for 20 minutes. The slices labelled with [$^3$H] noradrenalin were incubated in the presence of 0.1 μM 6-nitroquipazine and 0.1 μM GBR 12909, which are selective inhibitors of the uptake of serotonin and dopamine, respectively, in order to prevent possible false labelling of serotoninergic and dopaminergic synaptic endings.

For the same reasons, the slices labelled with [$^3$H] dopamine were incubated in the presence of 0.1 μM 6-nitroquipazine and 0.1 μM nisoxetine, which are selective inhibitors of serotonin and noradrenalin uptake. After incubation for 20 minutes, the slices were washed with aCSF in the absence of tracer and transferred into parallel perfusion chambers at a rate of one slice per chamber, and perfused at a speed of 1 ml per minute at a constant temperature of 37° C. After perfusion for 45 minutes to equilibrate the system, 9 fractions of 5 minutes each were collected. The test compounds were added to the perfusion liquid 10 minutes after the start of collection of the fractions. The percentage of tritiated neurotransmitter released from the slices into the first 2 fractions collected in the absence of drugs was considered as the internal control for each slice.

At the end of the experiment, the collected samples and the perfused slices (dissolved in toluene) were subjected to counting of the radioactivity present in each fraction and/or slice using a scintillator for liquid samples. The fractional release of tritiated neurotransmitters was calculated as the amount of radioactivity present in each fraction divided by the total radioactivity present in the slice at the moment at which it was collected. The ratios between the fractional release at a given moment of the perfusion and the fractional release in the first collected fraction were thus calculated for each slice. The effects of the compounds were expressed as a percentage of increase of the release of the neurotransmitters studied relative to the control slices perfused in the absence of drugs (Table 2). The data show the micromolar concentration of compound capable of increasing the basal release of neurotransmitters by 100%.

TABLE 2

Studies on the basal release of tritiated neurotransmitters from rat cerebral slices

| | Compound 2 (μM) | Compound 4 (μM) | Memantine (μM) |
|---|---|---|---|
| Basal release of [$^3$H]NE on hippocampus slices | 6 | 15 | 130 |
| Basal release of [$^3$H]DA on striatum slices | 2 | 8 | inactive (30 μM) |
| Basal release of [$^3$H]Ach on striatum slices | inactive (30 μM) | 20 | inactive (100 μM) |

From the data given in Table 2, it is seen that some of the compounds that are the subject of the invention, for instance compounds 2 and 4, are capable of increasing the basal release of NE and dopamine at micromolar concentrations. In contrast, memantine shows little or no activity, and is similarly inactive on the release of Ach. In contrast, compound 4 is very active also in increasing the release of the latter neurotransmitter into the corpus striatum.

b) Studies on the Release of [$^3$H] Noradrenalin Stimulated by N-methyl-D-aspartic Acid (NMDA) in Rat Hippocampus Slices The preparation of the slices is analogous to that described previously. The slices were perfused in the presence of [$^3$H] noradrenalin with an aCSF lacking in $Mg^{2+}$ ions. After perfusion for 45 minutes to equilibrate the system, 7 fractions of 5 minutes each were collected. The test compounds were added to the perfusion liquid 10 minutes before starting the collection of the fractions, while 100 μM NMDA was added only to fraction 4, from the fifteenth minute after the start of collection.

At the end of the experiment, the radioactivity present was counted as described previously. For each sample, the percentage ratio between the fractional release in fraction 4 in the presence of NMDA and the fractional release in the first collected fraction was determined. The activity of the test drugs was expressed as a mean percentage value of the number of experiments performed relative to the percentage increase in the release of [$^3$H] noradrenalin into the NMDA-stimulated control chambers in the absence of antagonists.

Some of the compounds that are the subject of the invention, for instance compounds 2 and 4, showed a powerful capacity to antagonize the effect of 100 µM of NMDA. Their $IC_{50}$ value was 0.8 and 0.5 µM. Memantine showed in this test a similar or slightly inferior activity, with an $IC_{50}$ value of 1.6 µM.

Neuroprotective Activity

Study of the Release of [$^3$H]D-aspartate Evoked by 30 mM of KCl Under Hypoglycaemic Conditions in Rat Parieto-occipital Slices.

This in vitro experimental model was designed to mimic a condition of neuronal pain and is a modification of the model reported by Zablocka B. and Domanska-Janik K., [NeuroReport 6, 85–88 (1994)].

Rat parieto-occipital cortex is removed and sectioned into 400 µm coronal slices. The cortical slices are incubated at 37° C. for 30 minutes with [$^3$H]D-aspartate and then, after washing for 45 minutes, stimulated for 5 minutes with a hypertonic potassium solution (30 mM). Once the basal conditions have been restored, the slices are perfused with a glucose-free medium for 20 minutes. The test compounds are at this point added to a standard medium containing glucose and perfused until the end of the experiment. 10 minutes from the end of the hypoglycaemic period, a further hypertonic potassium stimulation depolarizes the neuronal membrane, causing an approximately 75% increase in the release of [$^3$H]D-aspartate evoked under control conditions.

Compounds 2 and 4, and also the memantine used as comparative drug, were capable of completely antagonizing the hypoglycaemia-induced increase in the release of [$^3$H] D-aspartate. Compound 4 showed a more potent order of magnitude than memantine ($IC_{50}$: 0.8 µM vs 7.5 µM), while compound 2 showed intermediate potency ($IC_{50}$=2.5 µM).

NO-synthetase (NOS) Antagonist Activity a) The inhibitory activity on the formation of NO, measured as $NO_2^-$ (nitrite), was studied in vitro on culture media of rabbit articular chondrocytes stimulated with the cytokine IL-1β (1 ng/ml) for 48 hours. For the preparation of the chondrocytes, the method described by Berenbaum et al. [FEBS Letters 340, 51–55 (1994)] was followed. Briefly, fragments of sterilized cartilage from rabbit shoulder, ankle and knee articular heads were finely minced and digested at 37° C. with solutions of hyaluronidase, trypsin and collagenase to give, after filtration through sterile gauze and centrifugation at 600×g and suitable dilution with DMEM-FCS 10%, a concentration of about 1×10$^5$ cells per well.

The cells were maintained under these conditions to the point of confluency (about 15 days), the medium being changed every 3 days. At this point, the test products dissolved in the medium were added to each specimen and, 20 minutes later, 350 µl of IL-1β were added, to have a final concentration of 1 ng/ml. The stimulation lasted for 48 hours at 37° C. (incubation under air-7% $CO_2$). Next, an assay of the nitrites was performed on the cell supernatant according to the method described by Green et al. [Anal. Biochem. 126, 131–138 (1982)].

The results obtained are shown in Table 3, which gives, for some of the compounds that are the subject of the invention in comparison with memantine and L-NAME, a non-selective NOS inhibitor, the $IC_{50}$ value, i.e. the concentration (micromolar) of antagonist capable of inhibiting 50% of the formation of nitrite relative to the control group, i.e. relative to the cells stimulated with IL-1β but without the addition of antagonists.

TABLE 3

Compounds of formula:

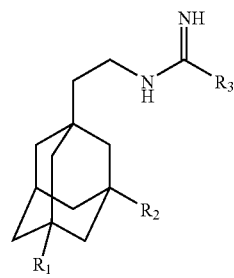

| Compound | $R_1$ | $R_2$ | $R_3$ | Rabbit articular chondrocytes % inhibition ($IC_{50}$ × 10$^{-6}$M) |
|---|---|---|---|---|
| 1 | H | H | $CH_3$ | 63.4 (42.1–95.5) |
| 2 | $CH_3$ | $CH_3$ | $CH_3$ | 25.5 (7.5–87.2) |
| 4 | $CH_3$ | $CH_3$ | $NH_2$ | 11.4 (5.5–23.5) |
| 5 | H | H | $NHNO_2$ | 30.7 (13.2–71.4) |
| 6 | $CH_3$ | $CH_3$ | $NHNO_2$ | 80.4 (41.9–154) |
| Memantine | — | — | — | IN (>300) |
| L-NAME | — | — | — | 340 (181–638) |

Note:
The confidence limits (95%) are given in parentheses

From the data given in the table, it may be deduced that some of the test compounds that are the subject of the invention show a potent inhibitory effect, at micromolar level, on the production of nitrite. The most active compounds are compounds 2 and 4, i.e. those in which $R_1$ and $R_2$ are methyl, n is 2 and $R_3$ is an amino or methyl group, respectively. The reference inhibitor compound L-NAME is about ten times less active, while memantine is entirely inactive up to the maximum concentration tested (3×10$^{-4}$M).

In Vivo Pharmacological Activity

Evaluation of the Antidepressant Activity

Another advantageous aspect of the pharmacological activity shown by these products is the potent antidepressant activity that some of them demonstrated in experimental models, in which a state of depression is induced experimentally.

a) Porsolt's Method

Process: The procedure is similar to that described by Porsolt et al. (Arch. Int. Pharmacodyn. 229, p. 327–336 (1977).

Naïve (unconditioned) mice are subjected to forced swimming for 15 minutes in a glass cylinder containing 20 cm of water at a temperature of 25° C. The period of immobility from the third to the sixth minute (inclusive) and the time to reach total immobility from the sixth to the fifteenth minute were measured. Total immobility is defined as the latent time required in order for the animal to remain immobile for at least 30 seconds. The compounds were administered orally 60 minutes before the test. Compound 4 showed potent antidepressant activity, reducing the period of immobility and increasing the latency to immobility at and above a dose of 1 mg/kg.

For doses of 1 and 10 mg/kg, these effects are statistically significant (P<0.05): amitryptiline, an inhibitor of NE re-uptake, was less active, since it only significantly increased (P<0.01) the latency to immobility at a dose of 30 mg/kg. The results obtained are given in Table 4.

TABLE 4

Effect of compound 4 and of amitryptiline in the swimming test (Porsolt) in the mouse

| | Compound 4 | | | | Amitryptiline | | |
|---|---|---|---|---|---|---|---|
| Dose (mg/kg) | Number of animals | Immobility in sec. (3–6 mins) | Latent time vs immobility in sec. (6–15 mins) | Dose (mg/kg) | Number of animals | Immobility in sec. (3–6 mins) | Latent time vs immobility in sec. (6–15 mins) |
| 0 | 20 | 66.6 | 281.6 | 0 | 12 | 56.9 | 387.5 |
| 0.1 | 8 | 39.3* | 353.3 | 3 | 8 | 54.9 | 477.5 |
| 1 | 20 | 39.8* | 450.8* | 10 | 8 | 56.0 | 461.0 |
| 10 | 8 | 42.4* | 495.8* | 30 | 8 | 42.0 | 607.8** |

*$P < 0.05$ vs control;
**$P < 0.01$ vs control b) "Tail Pinching" Test in the Mouse Process: The procedure is similar to that described by Steru et al. [Psychopharmacol. 85, p. 367-(1985)]. The animals are suspended by the tail 75 cm above the bench surface. The duration of immobility is measured over a period of 5 minutes: the animals are considered as being immobile only when they hang passively and completely motionless. The compounds were administered orally 30 minutes before the test. The results obtained are given in Table 5.

TABLE 5

Effect of compound 2 and of memantine in the "tail pinching" test in the mouse

| | Compound 2 | | | | Memantine | | |
|---|---|---|---|---|---|---|---|
| Dose (mg/kg) | Number of animals | Immobility time (sec.) | % effect vs control | Dose (mg/kg) | Number of animals | Immobility time (sec.) | % effect vs control |
| 0 | 25 | 76.2 | — | 0 | 10 | 78.9 | — |
| 0.3 | 15 | 56.6 | 25.7 | 0.1 | 10 | 49.9 | 36.8 |
| 1 | 5 | 48.0 | 37.0 | 1 | 10 | 48.9 | 38.0 |
| 3 | 15 | 42.6 | 44.1 | 10 | 10 | 40.1 | 49.2 |
| 10 | 15 | 35.1 | | | | 53.9 | |
| $ED_{50}$: 6.0 (4.2–8.7) mg/kg | | | | $ED_{50}$: 24.9 mg/kg | | | |

Compound 2 showed high antidepressant activity, reducing the immobility time of the animals over the 5 minutes of the experiment in a dose-dependent manner in the range 0.3–10 mg/kg. The calculated $ED_{50}$ was 6 mg/kg. Memantine is less active, its $ED_{50}$ being 24.9 mg/kg.

What is claimed is:

1. Compounds of general formula (I) given below:

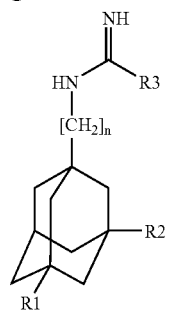

(I)

in which:
n is an integer between 1 and 4;
$R_1$ and $R_2$ are both methyl groups;
$R_3$ is chosen independently from a linear, branched or cyclic alkyl group containing from 1 to 3 carbon atoms ($R_{3a}$) and an unsubstituted amino group ($R_{3b}$) or an amino group substituted with a nitro group ($R_{3c}$), and pharmaceutically acceptable salts thereof.

2. Compounds according to claim 1 of formula (I) in which n is 2.

3. Compounds according to claim 2, in which $R_3$ is an amino group.

4. Pharmaceutical preparation comprising as active substance at least one of the compounds according to claim 1, or a pharmaceutically acceptable salt thereof.

5. Pharmaceutical preparation comprising as active substance at least one of the compounds according to claim 2, or a pharmaceutically acceptable salt thereof.

6. Pharmaceutical preparation according to claim 4, for use in the treatment of various pathological conditions of the central nervous system, for instance senile dementia, Alzheimer's disease, AIDS dementia-complex, behavioural disturbances and depression.

7. Pharmaceutical preparation according to claim 4, for use in the treatment of cerebral ischaemia.

8. Pharmaceutical preparation according to claim 4, for use in the treatment of peripheral neuropathies of either mechanical or metabolic origin.

9. Pharmaceutical preparation according to claim 4, for use in the treatment of degenerative inflammatory phenomena, for instance rheumatoid arthritis.

10. Pharmaceutical preparation according to claim 4, also comprising pharmaceutically acceptable inactive ingredients chosen from the group consisting of vehicles, binders, flavourings, sweeteners, disintegrating agents, preserving agents and humectants, and mixtures thereof, or ingredients that facilitate the parenteral, transdermal, transmucosal or rectal absorption or that allow controlled release over time of the active substance.

* * * * *